(12) United States Patent
Rau

(10) Patent No.: US 8,192,724 B2
(45) Date of Patent: Jun. 5, 2012

(54) ORAL CARE TABLET

(75) Inventor: Allen H. Rau, Cincinnati, OH (US)

(73) Assignee: Tower Laboratories, Ltd., Centerbrook, CT (US)

( * ) Notice: Subject to any disclaimer, the term of this patent is extended or adjusted under 35 U.S.C. 154(b) by 870 days.

(21) Appl. No.: 11/263,976

(22) Filed: Nov. 2, 2005

(65) Prior Publication Data

US 2006/0057078 A1    Mar. 16, 2006

Related U.S. Application Data

(63) Continuation of application No. 10/431,131, filed on May 7, 2003, now abandoned.

(51) Int. Cl.
*A61K 8/00* (2006.01)
(52) U.S. Cl. .......................... 424/49; 424/466; 424/53
(58) Field of Classification Search .................. 424/49, 424/466, 59
See application file for complete search history.

(56) References Cited

U.S. PATENT DOCUMENTS

| | | | | |
|---|---|---|---|---|
| 536,155 | A | * | 3/1895 | Noyes ........................... 424/466 |
| 834,676 | A | | 10/1906 | Luyties |
| 975,814 | A | | 11/1910 | Westlake |
| 1,411,681 | A | | 4/1922 | Burlew |
| 1,516,398 | A | | 11/1924 | Mc Dowell |
| 2,211,485 | A | * | 8/1940 | Zimmermann ............... 424/490 |
| 2,778,045 | A | | 1/1957 | Bly et al. |
| 3,116,208 | A | | 12/1963 | Emond |
| 3,431,339 | A | * | 3/1969 | Bouchal et al. ................. 424/52 |
| 3,497,590 | A | | 2/1970 | Eigen |
| 3,020,463 | A | | 12/1971 | Anderson |
| 3,962,417 | A | * | 6/1976 | Howell ........................... 424/52 |
| 4,267,164 | A | * | 5/1981 | Yeh et al. ........................ 424/44 |
| 4,308,252 | A | | 12/1981 | Tomaich et al. |
| 4,814,163 | A | * | 3/1989 | Barth ............................. 424/49 |
| 5,225,197 | A | * | 7/1993 | Bolt et al. ...................... 424/440 |
| 5,571,501 | A | * | 11/1996 | Toy ................................ 424/49 |
| 5,670,138 | A | | 9/1997 | Venema et al. |
| 5,804,165 | A | | 9/1998 | Arnold |
| 5,817,294 | A | | 10/1998 | Arnold |
| 5,869,095 | A | | 2/1999 | Gergely et al. |
| 5,965,110 | A | | 10/1999 | Arnold |
| 6,066,335 | A | | 5/2000 | Machoczek |
| 6,086,854 | A | * | 7/2000 | Arnold ............................. 424/44 |
| 6,254,856 | B1 | | 7/2001 | Tsuchiya |
| 6,355,228 | B1 | | 3/2002 | Fuglsang |
| 6,428,770 | B1 | * | 8/2002 | Kayane et al. .................. 424/44 |
| 2004/0126335 | A1 | | 7/2004 | Faller et al. |

FOREIGN PATENT DOCUMENTS

WO    WO/00/33800    6/2000
WO    WO 00/57858    10/2000

OTHER PUBLICATIONS

EP Exam Report 04751314.8, Jun. 29, 2010, Rau, Allen H.

* cited by examiner

*Primary Examiner* — Brandon Fetterolf
*Assistant Examiner* — Shirley V Gembeh
(74) *Attorney, Agent, or Firm* — Steven B. Kelber; Berenato & White, LLC

(57) ABSTRACT

A water soluble, non-abrasive, effervescent, pharmaceutically acceptable, oral care tablet for use in the oral cavity. The tablet includes a carbon dioxide source, a acid source and a tablet forming material admixed to form a chewable tablet having less than 0.2% water. The carbonate to acid ratio ranges from about 2.33:1 to about 3.33:1, the percent by weight of tablet forming material ranges from about 10% to about 70% of the total tablet weight, and the pH of the tablet when dissolved in water to form a 1.0% by weight aqueous solution ranges from about 5.0 to about 7.0. Also included is a flavor imparting flavor agent in an amount sufficient to mask taste sensations derived from the carbon dioxide source, acid source and binder to provide an abrasive-free texture to the tongue in the oral cavity. Other additives are contemplated.

4 Claims, No Drawings

ORAL CARE TABLET

This application is a Continuation of application Ser. No. 10/431,131 Filed on May 7, 2003 now abandoned

FIELD OF THE INVENTION

The present invention relates to oral care tablets. More particularly, the present invention relates to effervescent tablets intended for use in the oral cavity and that include one or more of anticaries agents, desensitizing agents, breath fresheners, antibacterials, whitening agents, prescription drugs and the like.

BACKGROUND OF THE INVENTION

Oral care products are available in many forms. Mouthwashes and fluoride rinses are typically liquids. Dentifrices are usually formulated as viscous gels pastes or powders. Breath fresheners can be found in tablet or strip form. Whiteners are typically provided in gel or gel-on-strip forms. Tablets, particularly chewable tablets, would seem to be an ideal product form for delivering functional ingredients to the oral cavity, particularly to the teeth and gums. This is so for several reasons. First, tablets are highly concentrated product forms and thus can carry high levels of solid ingredients. It can often be difficult to carry high levels of functional materials in liquid products as solubility limitations can cause product instability. Second, when tablets are chewed, the functional ingredients contained in them are placed in direct contact with the teeth. This allows excellent delivery of these materials to the tooth surface. Third, aesthetically, tablets provide an interesting sensory experience for the user. This is particularly true in the case of effervescent tablets. The gas releasing action of these products provides multisensory tactile and auditory stimulation to the user.

Many prior art patents show the general concept of providing a tablet or capsule that can be put in the mouth of a user for various purposes. Bly et al. U.S. Pat. No. 2,778,045 teaches the use of a capsule that is broken by the teeth to release a dentifrice. Alternatively the dentifrice may dissolve, followed by use of a brush. No foamable component is disclosed.

Also suggested is the use of the capsule itself as a brush. Emond U.S. Pat. No. 3,116,208 discloses a dental cleanser in tablet form. Calcium carbonate is mixed with sodium lauryl sulphate to bind together into a tablet that may be crushed by the teeth. The sodium lauryl sulphate is said to cause a foaming nature upon brushing the teeth.

Gyarmathy et al. U.S. Pat. No. 3,431,339 discloses a dental tablet for use in place of toothpaste. The tablet is said to be an intimate blend of water-soluble fluorine containing agents, polishing agents and foaming agents in a releasable matrix. Again, sodium lauryl sulphate is disclosed as one foaming agent. The patent suggests that fluorine and calcium are sometimes incompatible in toothpastes and this tablet solves that problem. The examples shown in the patent involve a great number of ingredients, and simplifying the tablet would be one significant advantage in the art. The patent also discloses hardness and thickness values.

Luyties U.S. Pat. No. 834,676 simply discloses that his formulation may be compressed into a tablet or lozenge form. Westlake U.S. Pat. No. 975,814 also simply discloses a tablet form as being preferred. Burlew U.S. Pat. No. 1,411,681 discloses a thin tablet that fits between the teeth of a toothbrush.

McDowell U.S. Pat. No. 1,516,398 discloses a chewing gum with a treating agent contained in a cavity in the gum. Elgen U.S. Pat. No. 3,497,590 teaches the improvement of using an aliphatic aldehyde or oxyderivative thereof for use in any dental product including both toothpaste and tablets, chewing gum, lozenges, etc.

Welsh et al. U.S. Pat. No. 3,518,343 discloses an effervescent tablet form cleaning the oral cavity by dissolution of the tablet in water. Tomaich et al. U.S. Pat. No. 4,308,252 discloses a tablet that is claimed to keep the active ingredients active for an extended period of time. The material is rehydrated into a viscous paste and is applied by a dental hygienist. Also, hardness is disclosed, but for narrower values than Gyarmathy et al. 3.5 to 4.0 versus 2.5 to 6.0, using different scales.

A series of four prior art patents relate to the use of chewable tablets. U.S. Pat. No. 5,804,165, to Arnold discloses an antiplaque oral composition using a source of carbon dioxide, silica and xylitol where the carbon dioxide comes from a bicarbonate. The effervescent tablet converts to a solid silica containing suspension in the saliva of an oral cavity. U.S. Pat. No. 5,817,294 is a continuation patent to Arnold that discloses a bicarbonate and acid, with silica or other solid materials, in a ratio of 0.32 to 1.0 to 0.8 to 1.0. U.S. Pat. No. 5,965,110 is a second continuation patent to Arnold in this series that discloses the carbon dioxide source and acid with silica and without the use of xylitol. Finally, the last Arnold continuation patent, U.S. Pat. No. 6,086,854, discloses the carbon dioxide source, the acid, xylitol and a precipitated amorphous silica. All four Arnold patents have an insoluble silica material as an abrasive The range of acid, such as citric acid, to bicarbonate ion is one part of acid to from about 1 to 20 parts of the latter, with 1.5 to 10 parts of bicarbonate atom per one part of fruit acid.

None of the prior art discloses a tablet for use with the oral cavity of a human in which the effectiveness of the tablet not only pleases the user but eliminates the use of any solid, nonsoluble material. Such a table would be an advance in the art.

One embodiment of the present invention is to provide an effervescent tablet that leaves a clean feeling in the mouth and can be used to carry a variety of functional ingredients to the oral cavity.

Another embodiment is to provide a tablet acceptable for consumer use, this tablet that must dissolve completely and quickly without grittiness, have a flavor that is not too salty or acidic and that is compatible with available flavors and sweeteners, and not be abrasive to the teeth, gums or any part of the mouth.

Another embodiment is to provide a tablet for a variety of oral cavity uses which does not have any solid material upon dissolution by chewing and mixing with saliva or other suitable liquids.

Other embodiments will appear hereinafter.

SUMMARY OF THE INVENTION

The present invention is admirable suited for use as a general tooth treating agent in tablet form. The base of the invention is an effervescent acid and a carbonate salt. The most frequently used acids are citric acid, fumaric acid, tartaric acid, malic acid and adipic acid. Other edible acids can be used. Sodium bicarbonate and sodium carbonate are the most commonly used carbonate salts. Potassium, ammonium, magnesium, calcium carbonate or other metal or organic salts can also be used as set forth below.

The present invention provides a tablet with water soluble functional ingredients that may include surfactants, anticaries agents, desensitizing agents, breath fresheners, antibacterials, whitening agents, and prescription drugs. An important aspect of the invention is that the tablet does not contain abrasive agents such as silica, silicate, aluminosilicate, or calcium phosphate so as to prevent damage to the teeth or gums. The pH of the tablet is designed to be slightly acidic to assure complete dissolution and so that its flavor does not become salty.

Formulating effervescent tablets that are intended for ingestion can be tricky. The balance of acidic and carbonate components must be managed carefully. If the carbonate compounds (such as sodium carbonate, sodium bicarbonate, potassium bicarbonate, potassium carbonate, calcium carbonate, and/or magnesium carbonate) are in too great an excess, the product can taste salty. Further, if these ingredients are present at too high a level the product pH will become too high for them to fully dissolve. This will cause grittiness and possibly abrasion to the teeth, gums and oral cavity surfaces. On the other hand, if the acidic materials are in too great an excess, the product may taste too bitter. Further, a highly acidic environment can damage the teeth.

The tablet includes a water soluble, non-abrasive, effervescent, pharmaceutically acceptable, chewable formulation for use in the oral cavity. The tablet includes a carbon dioxide source such as sodium bicarbonate, an acid source such as citric acid, a binder and lubricant mix such as sorbitol, with these components being admixed to form a chewable tablet having less than 0.2% water.

The carbonate to acid ratio preferably ranges from about 2.33:1 to about 3.33:1, the percent by weight of binder and/or lubricant ranges from about 10% to about 70% of the total tablet weight. Most important is that the pH of the tablet when dissolved in water to form a 1.0% by weight aqueous solution ranges from about 5.0 to about 7.0, and preferably about 5.5 to about 6.5.

Also included is a flavor imparting flavor agent such as citrus flavor and mint flavor, in an amount sufficient to mask taste sensations derived from the carbon dioxide source, acid source and binder to provide an abrasive-free texture to the tongue in the oral cavity. Other additives are contemplated. In a preferred embodiment, the tablet dissolves to produce a solids-free foal having a consistency similar to toothpaste during brushing.

DETAILED DESCRIPTION OF THE INVENTION

The present invention is a chewable tablet for use in the oral cavity to provide treatment of one or more aspects of oral hygiene and dental care. The base of the invention is a tablet incorporating an effervescent acid and a carbonate salt. The most frequently used acids are citric acid, fumaric acid, tartaric acid, malic acid and adipic acid. Of course, other edible acids can be used. Sodium bicarbonate and sodium carbonate are the most commonly used carbonate salts. However the potassium, ammonium, magnesium, calcium carbonate or other metal or organic salts can also be used.

As will be illustrated in following examples, the ratio of acid to carbonate is extremely important to the performance of the product. If the ratio is too acidic, the taste will be too bitter or tart. If there is excess carbonate, the product will taste salty and will not fully dissolve, leaving a gritty feeling in the mouth.

In addition to the acid/carbonate salt couple, the basic inventive tablet may contain various binders, fillers and/or lubricants. These materials should be chosen from among the well known materials that are used for these functions that are either water soluble or are not gritty when dispersed in water or saliva. Some examples of these materials are lubricants such as polyethylene glycol, polypropylene glycol, polyvinyl alcohol, polyvinyl pyrrolidone, sodium benzoate, leucine, magnesium stearate, sodium lauryl sulfate, and sodium lauryl sulfoacetate. Binders include sorbitol, lactose, urea, sucrose stearate, starch, maltodextrin, corn syrup solids, sodium citrate, sodium sulfate, sodium chloride, sucrose, dextrates, and the like. It is contemplated that the present invention will include either a binder or a lubricant or both. The term "tablet forming material" includes both binders and lubricants.

Excipients that modify the flavor and/or mouth feel of the product may also be incorporated in it. Examples of these materials are sweeteners such as calcium or sodium saccharin, aspartame, acesulfame potassium, sucralose, cyclamates, sucrose, glucose, dextrose, xylitol, manitol or other sugar, pectin, guar gum, gum arabic, xanthan gum, hydroxymethyl cellulose, hydroxypropyl cellulose, tragacinth gum, alginic acid or salts of alginic acid, and, of course, flavorants.

Flavor additives should be chosen carefully for use in this product. Since the product pH will be designed to be slightly acidic, flavors that are accentuated by acidity are preferred. Some examples of these types of flavors are citrus types (lemon, lime, orange grapefruit, etc.), ginger, various berries (raspberry, strawberry, blueberry, etc.) and mint types (peppermint, spearmint, wintergreen). Interestingly, these preferred flavor types can be combined with other flavor additives to yield an acceptably flavored product. Some examples of this situation are: spearmint/orange, cinnamon/clove/orange, and lemon/mint. Often the addition of a small amount of citrus flavoring will vastly improve the overall perception of the product's taste.

Functional additives can be incorporated in the base product. Examples of these materials and their functions are:

Anhydrous surfactants such as sodium lauryl sulfate, sodium lauryl sulfoacetate, cocamidopropyl betaine, sodium alpha olefin sulfonate, dioctyl sodium sulfosuccinate, and sodium dodecyl benzene sulfonate. These materials cause the product to generate foam. It will then function as a dentifrice.

Anticaries ingredients such as sodium fluoride, sodium monofluorophosphate and stannous fluoride. These materials are known to help prevent tooth decay.

Bleaching agents such as carbamide peroxide (also known as urea peroxide), sodium perborate, and sodium percarbonate. These materials can whiten teeth.

Enzymes such as papain and other proteases, amylases, and lipases can be used to help remove plaque and clean the teeth.

Desensitizing agents such as strontium nitrate and potassium nitrate. These materials reduce the unpleasant stimulation caused by heat or cold felt by many people on their teeth.

Antimicrobial agents such as cetylpyridinium chloride and domiphen bromide. These materials reduce the bacterial population of the oral cavity.

Breath freshening ingredients such as strong flavorings (see above), chlorophyll, and the antimicrobial ingredients listed above. These materials help reduce mouth odors by eliminating bacteria and by covering the odors with strong, typically minty, fragrances.

Other prescription medicines such as antibiotics and chlorhexidine gluconate.

Dyes used at levels that will color the foam generated by any surfactant that is incorporated in the product. This will add sensory interest to products designed for children.

Naturally, any material incorporated in this product will have to be of food or drug grade quality and should be safe for ingestion. Also, since effervescent products are chemically reactive (the acid combines with the carbonate salt to release water, carbon dioxide and the salt of the acid) by nature, it is very important that all materials used in them be essentially anhydrous. The maximum amount of moisture that, in general, can be incorporated in a well formulated effervescent product without inducing the effervescent reaction is 1%. Preferably this value is below 0.2%.

In order to demonstrate the efficacy of the present invention, a number of experiments were run. The tablet making procedure used for the first set of experiments is as follows: Add the flavor oil (in the case of menthol/eucalyptol product, first dissolve menthol crystals in eucalyptol) to the dextrates, sucrose, or sorbitol. Mix well to distribute the oil uniformly on the substrate. Add the balance of the excipients and mix until uniform. Press into the desired size and weight tablets using conventional tablet making equipment. The typical size tablet will be between 0.25 grams and 3.0 grams. Presented below in Table I are the results of a plurality of formulations for breath fresheners, with all components expressed in weight of ingredient per total weight. Similarly, Table II presents examples of effervescent detnifrices.

TABLE I

EFFERVESCENT BREATH FRESHENERS

| material | A | B | C | D | E | F |
|---|---|---|---|---|---|---|
| citric acid | 15.0 | 15.0 | 15.0 | 15.0 | 15.0 | 7.5 |
| sodium bicarbonate | 25.0 | 30.0 | 30.0 | 40.0 | 35.0 | 17.5 |
| mint flavor | 1.0 | 1.0 | — | — | — | — |
| peppermint oil | — | — | 1.0 | 2.0 | 2.0 | 2.0 |
| sodium saccharin | 1.0 | 1.0 | 2.0 | 2.0 | 2.0 | 2.0 |
| PEG-180 | 2.0 | 2.0 | 2.0 | 2.0 | 2.0 | 2.0 |
| dextrate | 56.0 | 51.0 | 50.0 | 39.0 | 44.0 | 69.0 |
| TOTAL | 100.0 | 100.0 | 100.0 | 100.0 | 100.0 | 100.0 |
| carb/acid ratio | 1.67:1 | 2:1 | 2;1 | 2.67:1 | 2.33:1 | 2.33:1 |
| total effervescence level | 40% | 45% | 45% | 45% | 50% | 25% |
| pH | 4.9 | 5.4 | 5.4 | 5.7 | 5.5 | 5.5 |
| results | bitter | slightly tart | slightly tart | slightly tart | too fizzy | good |

| material | G | H | I | J | K | L |
|---|---|---|---|---|---|---|
| citric acid | 7.5 | 7.5 | 7.5 | 7.5 | 7.5 | 7.5 |
| sodium bicarbonate | 20.0 | 25.0 | 25.0 | 25.0 | 25.0 | 25.0 |
| menthol | 1.0 | 1.0 | 1.0 | — | — | — |
| eucalyptol | 1.0 | 1.0 | 1.0 | — | — | — |
| winter mint flavor | — | — | — | 2.0 | 2.0 | — |
| lemon flavor | — | — | — | — | — | 2.0 |
| sodium sacharin | 2.0 | 2.0 | — | — | — | — |
| aspartame | — | — | 2.0 | 2.0 | 1.0 | 2.0 |
| acesulfame-K | — | — | — | — | 1.0 | — |
| PEG-180 | 2.0 | 2.0 | 2.0 | 2.0 | 2.0 | 2.0 |
| sucrose | 66.5 | 61.5 | 61.5 | — | — | — |
| sorbitol | — | — | — | 61.5 | 61.5 | 61.5 |
| TOTAL | 100.0 | 100.0 | 100.0 | 100.0 | 100.0 | 100.0 |
| carb/acid ratio | 2.67:1 | 3.33:1 | 3.33:1 | 3.33:1 | 3.33:1 | 3.33:1 |
| total effervescent level | 27.5% | 32.5% | 32.5% | 32.5% | 32.5% | 32.5% |
| pH | 4.4 | 5.6 | 5.7 | 5.7 | 5.7 | 5.7 |
| results | slightly bitter | good | good | good | good | good |

TABLE II

EFFERVESCENT DENTIFRICES

| material | A | B | C | D | E | F |
|---|---|---|---|---|---|---|
| citric acid | 10.0 | 20.0 | 20.0 | 20.0 | 20.0 | 20.0 |
| sodium bicarbonate | 30.0 | 50.0 | 45.0 | 60.0 | 60.0 | 60.0 |
| calcium carbonate | — | — | 10.0 | — | — | — |
| sodium lauryl sulfate | 1.0 | 1.0 | 1.0 | 1.0 | 1.0 | 1.0 |
| spearmint flavor | 0.8 | 0.8 | 0.8 | 0.8 | — | 0.8 |
| orange flavor | 0.2 | 0.2 | 0.2 | 0.2 | 0.1 | 0.2 |
| cinnamon clove flavor | — | — | — | — | 0.1 | — |
| sodium saccharin | 2.0 | 2.0 | 2.0 | 2.0 | 2.0 | — |
| aspartame | — | — | — | — | — | 1.0 |
| accsulfame-K | — | — | — | — | — | 1.0 |
| pectin | — | — | 0.5 | — | — | — |
| PEG-180 | 2.0 | 2.0 | 2.0 | 2.0 | 2.0 | 2.0 |
| sorbitol | 54.0 | 24.0 | 18.5 | 14.0 | 14.8 | 14.0 |
| TOTAL carb/acid ratio | 3:1 | 2.5:1 | 2.75:1 | 3:1 | 3:1 | 3:1 |
| total effervescence level | 40% | 70% | 75% | 80% | 80% | 80% |
| pH | 5.9 | 5.7 | 5.8 | 5.9 | 5.9 | 5.9 |
| results | too little fizz | too tart | slight tart | good | good | good |

Table III, below, illustrates additional effervescent formulations that have been proved to produce the clean feel of the present invention.

TABLE III

ADDITIONAL EFFERVESCENT FORMULATIONS

| material | | desensitizing tablet | fluoride dentifrice | whitening tablet | antimicrobial tablet |
|---|---|---|---|---|---|
| citric acid | | 20.00 | 20.00 | 12.00 | 15.00 |
| sodium | bicarbonate | 60.00 | 60.00 | 36.00 | 45.00 |
| sodium | lauryl sulfate | — | 1.00 | — | — |
| potassium | nitrate | 5.0 | — | — | — |
| sodium | fluoride | — | 0.24 | — | — |
| carbamide | peroxide | — | — | 10.00 | — |
| chlorohexadine | gluconate | — | — | — | 0.12 |
| flavor | | 0.50 | 0.50 | 0.50 | 0.50 |
| aspartame | | 2.00 | 2.00 | 2.00 | 2.00 |
| PEG-180 | | 2.0 | 2.0 | 2.0 | 2.0 |
| sorbitol | | 10.5 | 14.26 | 37.5 | 35.38 |
| TOTAL | | 100.00 | 100.00 | 100.00 | 100.00 |

It should be noted that none of the examples shown above incorporate materials that could be abrasive to the teeth. Even when insoluble materials such as calcium carbonate are used, the pH of the product is adjusted so that the material becomes soluble. This is done without dropping the pH to a level which could be damaging to the teeth. Further, it should be noted that the effervescent combinations of acid and carbonate presented above leave a pleasant, clean feeling on the tooth surface and in the mouth. This feeling is unexpected and is not predicted by the prior art. It is also preferred that the tablet dissolve as noted, using the effervescence, to produce a solids-free foal having a consistency similar to toothpaste during brushing.

In summary, it can be seen that a carefully balanced effervescent tablet has been discovered for delivering functional materials to the oral cavity. The invention differs from previously known products in that it avoids the use of abrasive and potentially gritty materials such as silica, silicon dioxide, aluminosilicate or calcium phosphate. Further, the consumer will enjoy using the product because the taste will be acceptable.

While particular embodiments of the present invention have been illustrated and described, it is not intended to limit the invention, except as defined by the following claims.

The invention claimed is:

1. A tablet composition for use in the oral cavity of a user, comprising a combination of an acid component and a carbonate salt component which, when dissolved together in the oral cavity, combine to effervesce, wherein said acid component is selected from the group consisting of citric acid, fumaric acid, tartaric acid, malic acid, adipic acid and mixtures thereof, and said carbonate salt component is selected from the group consisting of sodium carbonate, sodium bicarbonate, potassium carbonate, ammonium carbonate, magnesium carbonate, calcium carbonate and mixtures thereof; total carbonate component and total acid component being present in amounts of 2.33:1 to 3.33:1, carbonate component to acid component said tablet, when dissolved in water to form a 1.0% by weight aqueous solution, providing a pH to said aqueous solution of about 5.0 to 6.5; said tablet further comprising a flavoring agent, a binder and a lubricant, wherein said tablet is free of materials that are abrasive to the oral cavity of the user.

2. The tablet of claim 1, wherein said tablet has a moisture content of below 1.0%.

3. The tablet of claim 2, wherein said moisture content is below 0.2%.

4. The tablet of claim 1, wherein said tablet is between 0.25 and 3.0 grams in weight.

* * * * *